June 29, 1976 MARIE-LOUISE MEILLAND et al. Plant Pat. 3,926
ROSE PLANT-MEINASTUR
VARIETY
Filed Oct. 24, 1974
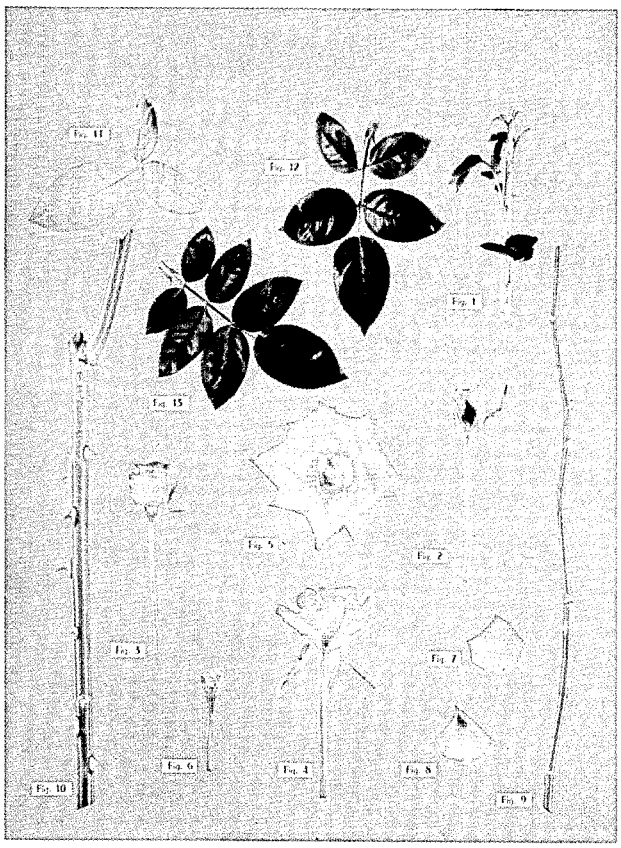

United States Patent

Plant Pat. 3,926

Patented June 29, 1976

3,926

ROSE PLANT—MEINASTUR VARIETY

Marie-Louise Meilland and Alain A. Meilland, Antibes, and Michele Meilland Richardier, Tass-in-la-Demi-Lune, France, assignors to The Conard-Pyle Company, West Grove, Pa.

Filed Oct. 24, 1974, Ser. No. 517,818

Claims priority, application Morocco, Dec. 7, 1973, 16,624

Int. Cl.[2] A01H *5/00*

U.S. Cl. Plt.—20 1 Claim

ABSTRACT OF THE DISCLOSURE

A new and distinct variety of rose plant of the hybrid tea class, originated by crossing unnamed and unpatented seedlings, and obtaining a bright vermilion color of its flowers, with great aptitude of the plant for forcing.

SUMMARY OF THE INVENTION

The object of the present invention is a variety of rose plant of the hybrid tea class, with semi-double vermilion flowers, which is distinguishable from varieties already known in that class and in that color, because of the following characteristics:

particularly attractive originality of the bright vermilion color of its flowers;
great aptitude of the plant to forcing; and
good steadiness of growth of the forced plants.

Because of the characteristics mentioned above, the present invention answers the needs of the horticultural industry, for all uses, and more particularly for the production of cut flowers.

The aim of the applicants was to create a variety which would derive the aforementioned advantages from the genetic combination of two genitors whose previous and respective study would allow them to expect, in their common descent, the appearance of the characters sought.

The rose chosen as female genitor was an unnamed and unpatented product of the pollination of a yet unknown variety born of a crossing made between the variety Show Girl and the variety Meger–561, more generally known in the trade under the name of Baccara, by the variety Meialto–219F, more generally known in the trade by the name of Romantica; the rose chosen as male genitor was the product of the pollination of the variety Meialto–219F, more generally known in the trade under the name of Romantica by the variety Tanorstar, more generally known in the trade under the name Super Star.

The operation of artificial pollination performed by the applicants therefore can be expressed by the following schematic formula:

$$\text{Show Girl} \times \frac{\text{Meger–561}}{\text{Baccara}} \times \frac{\text{Meialto–219F}}{\text{Romantica}} \times \left(\frac{\text{Meialto–219F}}{\text{Romantica}} \times \frac{\text{Tanorstar}}{\text{Superstar}}\right)$$

From the fruits thus formed by this controlled pollination, seeds were extracted whose cells were the result of the combination of factors which existed in the cells of the genitors and in virtue of which these genitors had been precisely chosen.

After having sown these seeds the applicant obtained 490 small plants, physically and biologically distinct from one another.

After having eliminated all the plants which were deficient or abnormal, or whose characters were too remote from the ones they were seeking, the applicants proceeded with the grafting of the remaining plants, in order to carry on their work exclusively on rose plants which were, in every respect, in conformity with those produced and commercialized by professional nurserymen.

From then on, they undertook the selective study of the plants thus formed, during which study they were led to eliminate systematically all the rose plants which had been grafted, with the exception of one only, which came the closest to the desired goal.

This variety was endowed with a bright vermilion color, original and attractive, and showed great aptitude to forcing.

Technical tests (grafting inside or outside, with dormant eye-buds, started eye-buds, in heated glasshouses, in cold glasshouses, on various understocks) were then made so as to ascertain the behavior of the variety just created.

The results were conclusive and underlined the importance of creating this variety with a view to its industrial exploitation for all uses, especially for the production of cut flowers.

The characters and properties of this new variety, obtained as indicated above, are strictly transmissible by agamic means, also called asexual, i.e. by any means of vegetative propagation, and in particular by grafting an "eye" which will be designated in the trade by the name of eye of Meinastur 0852F and which will be found on industrial plants as well as on cut stems delivered subsequently in the trade. Thus will be obtained once again the new rose variety and whose botanical and descriptive characteristics, observed on glasshouse plants, are given below:

BRIEF DESCRIPTION OF DRAWINGS

The accompanying drawings show as nearly true as it is reasonably possible to make the same in a color illustration of this character, typical specimens of the flowers and foliage, illustrating in FIG. 1 a specimen of a young shoot;

FIG. 2 a specimen of a bud when sepals open;

FIG. 3 a specimen of a bud when petals open;

FIG. 4 a specimen of a flower in the course of opening;

FIG. 5 a specimen of a fully open flower, flat view, upper surface;

FIG. 6 a specimen of a receptacle showing the disposition of the stamens and of the pistils;

FIG. 7 a specimen of petal of the outer periphery of the flower, with a pointed tip and reflexed lateral edges, inner surface;

FIG. 8 a specimen of petal of the outer periphery of the flower, with a pointed tip and reflexed lateral edges, outer surface;

FIG. 9 a portion of a flowering branch;

FIG. 10 a portion of a main branch;

FIG. 11 a specimen of leaf with three folioles, under surface;

FIG. 12 a specimen of leaf with five folioles, upper surface; and

FIG. 13 a specimen of leaf with seven folioles, upper surface.

DETAILED DESCRIPTION OF DISCLOSURE

The chart used for the identification of the colors is that of the Royal Horticultural Society (R.H.S. Color Chart). The terminology preceding the numbered references, proper to this chart, has been added to designate, in common terms, the corresponding colors.

CLASS: Hybrid tea

PLANT: Development: considering the plants having been cut back to .85 m., the length of the flowering stems will be between 50 to 70 cms.

Habit: erect

BRANCHES:

Color: young stems: before buds are formed, they are light green on the shaded side, reddish purple on the sunny side; as and when buds form, they turn to bronze green, then to light green 146/C (yellow-green group); mature wood: medium green 146/A (yellow-green group)

Prickles: shape: upper edge: straight, inflexed towards the base; under edge: concave, base: obovate, narrow; size: medium to small; quantity: medium to small, they are sometimes intermixed with needle-shaped points on the very vigorous branches; color: on young stems: before buds are formed, they are light reddish purple; then in succession, they turn to greenish with a pink point, and to greenish and light straw (common terms); on mature wood: light havana (common term)

LEAVES:

Stipules: adnate, pectinate, narrow and linear

Petiole: obverse: the inside and edges of the rib are reddish brown in the young foliage, medium green in the adult foliage; the edges are generally slightly, to very slightly glandular; reverse: light green, with small prickles, hooked and greenish white; position: it forms with the stem an angle between 45 and 90°

Folioles: number: 3–5–7; shape: on a standard model leaf, on the average ⅓ of a flower-bearing branch (1st pair starting from the top); base: rounded, asymmetrical; top: wide, symmetrical; general shape: elliptical; teeth: single and fine; texture: leathery; general effect: ample foliage, medium dense, shiny on young stems before the buds are formed; semi-dull afterwards; color: young foliage; upper surface: dark green 147/A (yellow-green group), shiny; under surface: light green, between 191/A and 191/B (greyed-green group) sometimes lightly satin-like reddish; adult foliage; upper surface: dark green 147/A (yellow-green group) semi-dull; under surface: light green between 191/A and 191/B (greyed-green group)

It is to be noted that when growth starts, as also during the course of vegetation, the foliage of the young shoots is reddish purple on the upper and under surface.

INFLORESCENCE:

Number of flowers: one flower per stem

Peduncle: straight, sometimes, however, it is plainly curved close to the receptacle, its surface is very slightly thorny, it is light green; length: 11 cms. on an average; sepals: downy, greenish white inside, light green and smooth outside, the tips are narrow and tapered, the edges usually have a few appendages; bud: shape: when sepals open, it is pointed and gradually takes on a cylindrical shape until the opening of the first petals; length: average 30 cms. outside of the calyx, as soon as the sepals open; size: medium; color: at the opening—inside: vermilion 44/A (red group), outside: vermilion 46/C (red group) more or less shaded with 46/A

FLOWER:

Form: first of all, high, full center, still keeping the cylindrical shape of the bud, whereas the outer petals, already well developed, are gradually joined by the center ones, always projecting; the flower then opens as a cup, somewhat flattened out; the stamens are conspicuous Semi-double flower: diameter: 10 cms. on an average; color: when opening: inside: vermilion 44/A (red group), bright, outside: carmine lake 46/D (red group); in the course of opening: inside: bright vermilion between 44/A and 44/B (red group) and tending to lighten to more of an orange red as the blossom ages; outside: Crimson 52/A (red group); when fully open: inside: vermilion between 44/A and 44/B (red group) becoming gradually mat, outside: crimson 52/B shaded with 52%A (red group) near the edges Fragrance: nil Lasting quality when cut: long Corolla: petals: texture: very firm, the unguis is yellowish white with a Rose Neyron aureole 55/A (red group) more spread outside than inside; shape: round, flat, tip in a point, reflexed lateral edges; number: 20; the petals drop off cleanly; stamens: number: 130 on an average, anthers: normal, yellow, filaments: whitish, more or less tinted with Carmine; pistils: number: 90 average; stigmas: yellowish, distinctly over the orifice of the receptacle and over the anthers; styles: long, yellow at base, reddish at top, downy; receptacle: light green, lengthwise it is narrow and funnel-shaped; when mature, the fruit is more or less pear-shaped and a few ovaries sometimes develop on the outside; it is orange in color 30/C (orange-red group).

DEVELOPMENT:

Vegetation: very vigorous

Flowering: practically continuous

Resistance to diseases: good

We claim:

1. A new and distinct variety of rose plant of the hybrid tea class substantially as illustrated and described, distinguished as to novelty, from the physical point of view, the plant, with medium green adult wood, is erect, the flower is semi-double, bright vermilion inside, crimson outside, the petals are very firm and show a yellowish white unguis, from the biological point of view, this rose plant is of vigorous growth, has great aptitude to forcing, its flowers last a long time when cut and their petals drop off cleanly.

No references cited.

ROBERT E. BAGWILL, Primary Examiner